US 6,715,904 B2

(12) United States Patent
Naughton

(10) Patent No.: US 6,715,904 B2
(45) Date of Patent: Apr. 6, 2004

(54) LASER LIGHT HANDLE

(76) Inventor: Michael L. Naughton, 2876 S. Wheeling Way, Aurora, CO (US) 80014

( * ) Notice: Subject to any disclaimer, the term of this patent is extended or adjusted under 35 U.S.C. 154(b) by 317 days.

(21) Appl. No.: 09/909,632

(22) Filed: Jul. 19, 2001

(65) Prior Publication Data

US 2003/0014834 A1 Jan. 23, 2003

(51) Int. Cl.$^7$ ............................................. F21V 21/08
(52) U.S. Cl. ........................ 362/399; 362/259; 362/109; 362/234; 362/804
(58) Field of Search ..................... 362/399, 400, 362/253, 804, 109, 259, 295, 234; 16/421

(56) References Cited

U.S. PATENT DOCUMENTS

| | | | |
|---|---|---|---|
| 4,605,124 A | 8/1986 | Sandel et al. | 206/223 |
| 4,974,288 A | 12/1990 | Reasner | 16/114 R |
| 6,056,414 A | * 5/2000 | Krieger | 362/184 |
| 6,149,286 A | * 11/2000 | Wiggins | 362/259 |
| 6,238,119 B1 | * 5/2001 | Liu | 401/195 |

OTHER PUBLICATIONS

Brochure, Devon Industries, "Light Handle System", Graphic Controls Corporation, 3 pages, 1998.

* cited by examiner

Primary Examiner—Sandra O'Shea
Assistant Examiner—Ali Alavi
(74) Attorney, Agent, or Firm—Sheridan Ross P.C.

(57) ABSTRACT

A light handle of an illuminating light is provided which produces a directed beam of light in order to precisely orient and align the illuminating light on a work area. Preferably, a laser producing light source is incorporated within the handle housing, and the directed beam of laser light projects from the distal end of the light handle. The laser light source may be battery powered, or may be powered by a solar panel mounted to the light handle; the illuminating light providing sufficient light to power the solar panel. To maintain sterility in a surgical environment, a light handle cover may be mounted to the light handle. For non-sterile applications, the light handle may simply be attached to the illuminating light without the light handle cover.

20 Claims, 3 Drawing Sheets

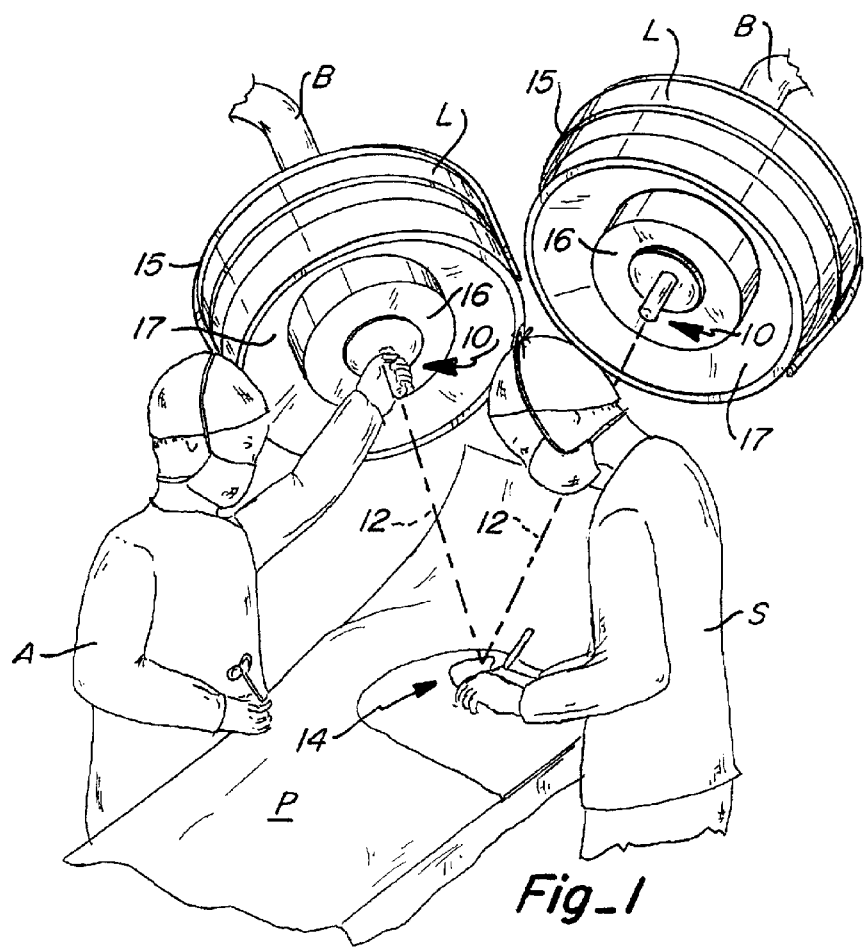
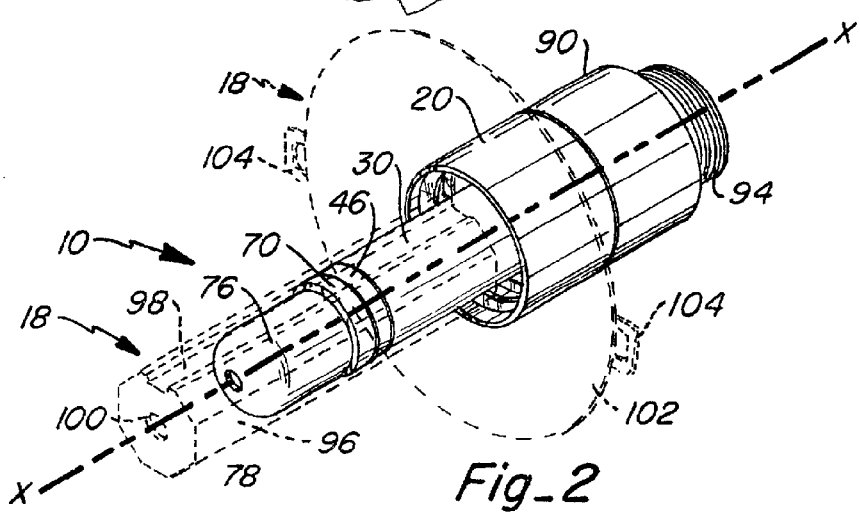

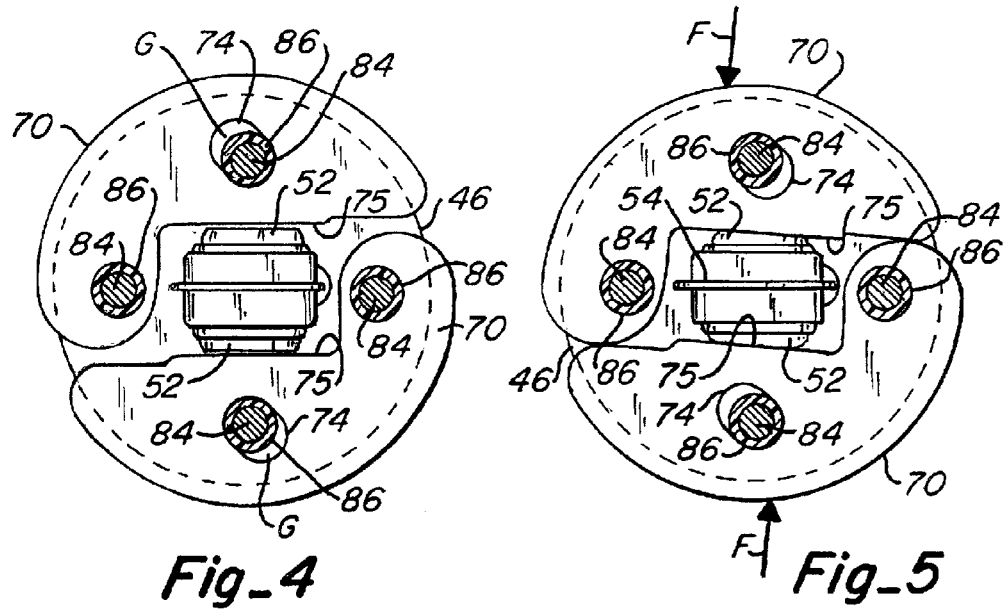
Fig_4    Fig_5
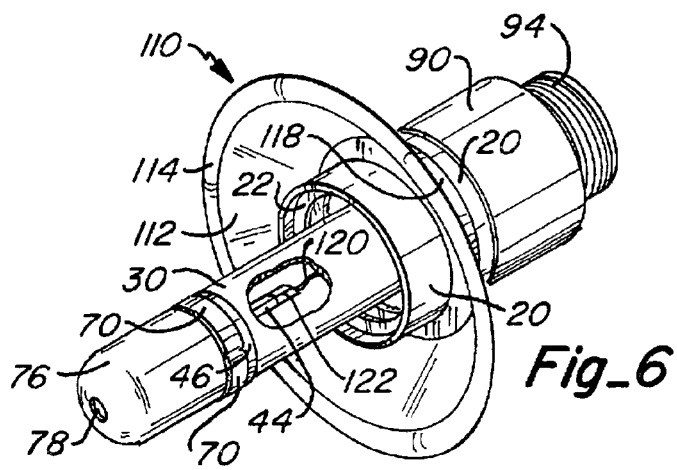
Fig_6
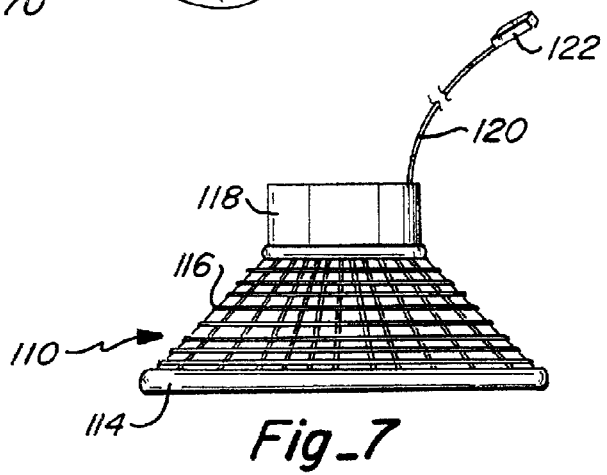
Fig_7

LASER LIGHT HANDLE

FIELD OF THE INVENTION

This invention relates to a device which provides a directed beam of light for alignment of another device, and more specifically, to a laser light source which is incorporated within the handle of a surgical light wherein the light handle itself acts as a pointing device to properly orient the surgical lights on a surgical area.

BACKGROUND OF THE INVENTION

Surgical lights are used in surgical procedures to provide the appropriate amount of illumination so that a surgeon and other operating room personnel can clearly see the surgical area. In any surgical procedure, it is critical that the surgeon and other operating room personnel have a clear unobstructive view of the surgical area in order that the surgical procedure be carried out without distractions created by poor lighting conditions. Typically, surgical lights produce a light pattern that is brightest in the middle and then diminishes toward the exterior edges of the light pattern. At the exterior edges of the light pattern, the brightness may be reduced by as much as 80% in comparison to the middle of the light pattern. Human tissue, particularly human tissue within a surgical cavity, absorbs most of the light which it is exposed to. Accordingly, it becomes exceedingly difficult to adequately illuminate many surgical cavities. Additionally, many surgical cavities have overlapping tissues which create shadows thus making proper viewing of the surgical cavity more difficult. Surgical lights are extremely bright in comparison to most other lights used for indoor illumination. Typically, surgical lights have an output of 11,000 foot candles or higher. Also, surgical lights are commonly used in tandem to overcome any shadow effects which may be caused by a single light itself, or by conditions within the surgical cavity. The surgical lights must be properly oriented over the surgical area to maximize the illumination of the lights.

Although human tissue reflects very little light, the various coverings and wraps placed around the surgical area reflect much more light. In order to minimize glare produced by light reflected from the area surrounding the surgical area, it is desirable to exactly position the surgical lights so that the middle portion of the light patterns directly intersect with the surgical area. Improperly aligned surgical lights can result in inadequate illumination of the surgical area and increased glare. These conditions can produce eye fatigue and can disrupt efficient handling of the surgical procedure.

Most surgical lights have a single, centrally located handle which coincidentally defines the geometric center of the light and thus, the center of the light pattern produced by the light. The handle of a surgical light is made sterile by providing the handle with a disposable cover which is replaced after each surgical procedure. Operating room personnel to include the surgeon may grasp the light handle many times during a surgical procedure to best orient the light during the procedure.

An example of a disposable cover for a surgical light handle includes the U.S. Pat. No. 4,605,124. This reference also illustrates a common surgical light. This patent is hereby incorporated by reference for purposes of disclosing not only typical surgical lights, but also a light handle cover which is used to cover a centrally located light handle. Another example of a disposable cover for the light handle of a surgical light includes the U.S. Pat. No. 4,974,288. While these references disclose a single centrally located light handle, there are no means provided to directly aim the surgical light at its intended target.

SUMMARY OF THE INVENTION

From the foregoing, it is apparent that a need exists for having the capability to orient surgical lights on their intended target within the surgical area.

The invention disclosed and claimed herein provides an aiming device which is incorporated within the light handle to efficiently and quickly orient surgical lights. As further discussed below in connection with the preferred embodiment, a laser light handle is provided which combines a laser light source within the light handle of the surgical light. A directed beam of laser light is transmitted from the distal tip of the laser light handle by operating a switch which turns the laser light on or off. The laser light may be powered by a battery housed within the light handle, or solar power can be used to power the laser by incorporating a thin film solar panel mounted around the light handle. The solar panel receives light from the surgical light(s). The laser light beam is of a sufficient brightness which makes it clearly distinguishable from light produced by the surgical lights. In order to orient the surgical lights, the surgeon or other operating room personnel simply grasp the surgical light by the light handle, then adjust the positioning of the light to direct the laser light beam on the target. The laser light beam appears as a very bright spot of light on the target. Since the light handle is centered within the surgical light, the spot of laser light acts as a simple pointer to exactly align the light pattern of the surgical light on the target.

If the light handle is to be used in a sterile procedure, a light handle cover is used to cover the light handle. The light handle cover is modified to include a small opening which allows the directed beam of laser light to reach its target. The switch includes a unique arrangement on the exterior surface of the light handle which enables the user to easily activate or deactivate the laser light source. This switch may also be centered along identifiable exterior features of the light handle cover thus enabling the user to activate the laser light by touch alone, while keeping eyes centered on the target.

The proximal end of the light handle may include one or more adaptors which allow it to be used with different types of surgical lights. Accordingly, the light handle of this invention is not restricted to use with any particular type of surgical light.

While the invention disclosed and claimed herein has particular utility with respect to surgical lights, the invention herein also lends itself to use in many other fields. In any endeavor requiring the use of an illuminating light which needs to be centered over a particular work area, the light handle of this invention may be used to orient the illuminating light on its target. Because of its cylindrical shape, the light handle acts as a pointer which can be directed for aligning an illuminating light.

Various other advantages will become apparent in conjunction with the detailed description, taken in conjunction with the accompanying drawings.

BRIEF DESCRIPTION OF THE DRAWINGS

FIG. 1 is a perspective view illustrating a pair of surgical lights used to illuminate a surgical area attended to by a surgeon and a surgeon's assistant, the surgical lights each incorporating the laser light handle of the invention;

FIG. 2 is a perspective view of the laser light handle of this invention, and an example of a light handle cover (in dotted lines) mounted over the light handle;

FIGS. 4 and 5 are enlarged elevation views of the switch which is used to activate/deactivate the laser light, and the switch activation members used to operate the switch;

FIG. 6 is another perspective view of the light handle, but incorporating a solar module as an alternate source of power for powering the laser light; and FIG. 7 is a side elevation of the solar module separated from the light handle further illustrating the details thereof.

DETAILED DESCRIPTION OF THE INVENTION

Figure 3:
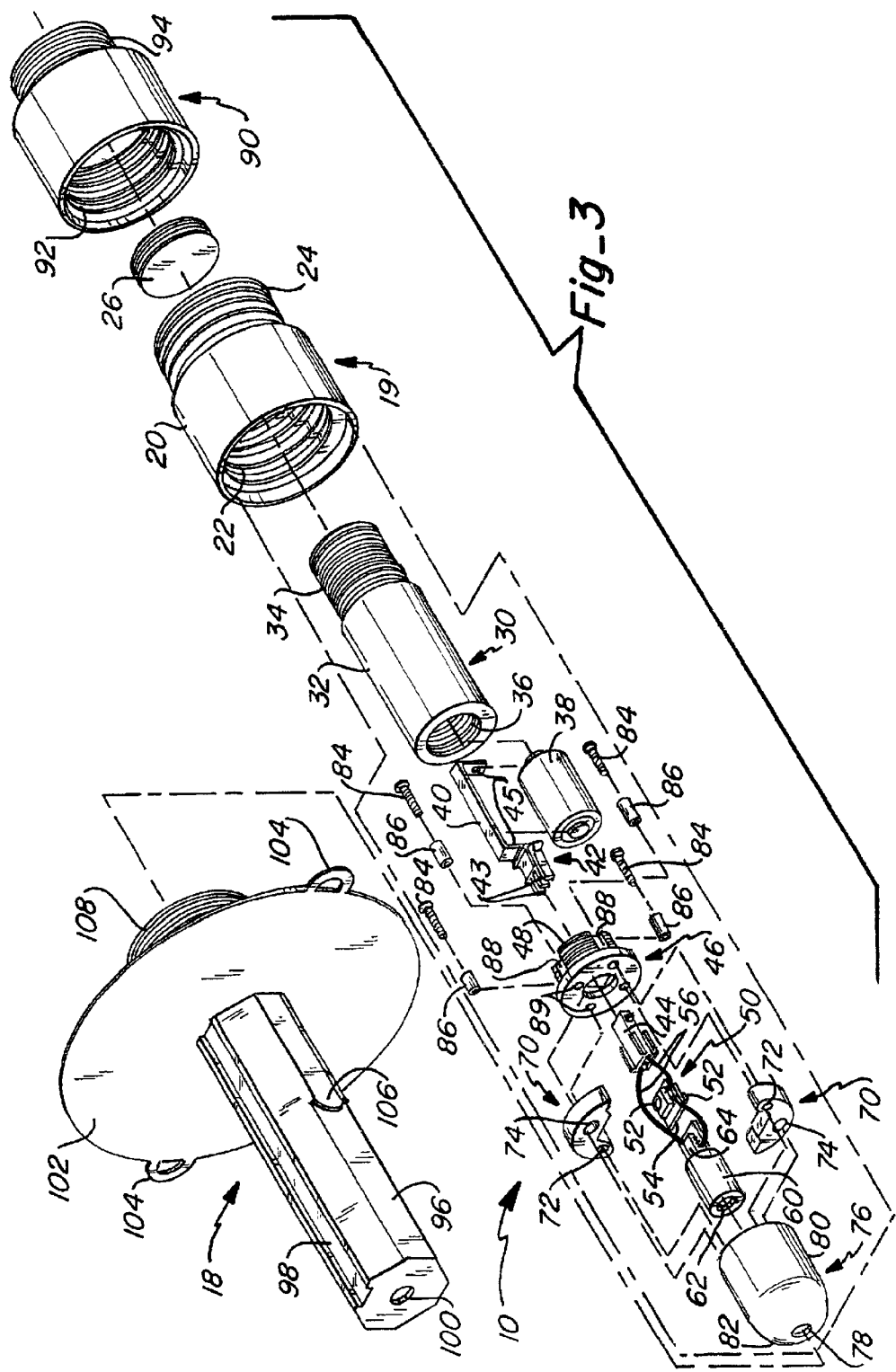
FIG. 3 is an exploded perspective view illustrating the details and components of the surgical light handle, and a perspective view of the light handle cover.

FIG. 1 illustrates the light handle of the invention 10 used in conjunction with surgical lights L which are mounted upon adjustable brackets B. As shown, a surgeon S and an operating room assistant A are conducting a surgical procedure on a patient P. The lights L are directed or pointed in alignment with a surgical area or site 14. Light handles 10 are mounted to each light L, and are aimed directly at the surgical site 14. Each of the light handles 10 can produce a directed beam of light 12 to the surgical site 14 which results in precise alignment of the surgical lights L. FIG. 1 also shows the simple manner in which the light handle L may be activated. As shown, the operating room assistant A simply reaches up and grasps the light handle 10, and then selectively activates/deactivates the light handle 10 to produce the directed beam of light 12 to align the corresponding surgical light L onto the surgical area 14.

It shall be understood that surgical lights L and brackets B represent common or generic surgical lights and the lights L are adjustable either by brackets B or some other known mechanical linkage. With respect to the specific style of lights shown in FIG. 1, each of the lights L include a housing 15, an opaque central portion 16 which serves as a mounting structure for a corresponding light handle 10, and an annular light emitting portion 17 which includes a plurality of lamps or other light emitting elements which illuminate the surgical area 14 in a round light pattern.

FIG. 2 illustrates the light handle 10 prior to mounting on the lights L, and a light handle cover 18 (illustrated in dotted lines) which may be mounted over the light handle 10 in order to provide sterile conditions for surgical procedures. The light handle cover 18 simply fits over the distal end of the light handle 10, as further discussed below.

The light handle cover 18 can be a commercially available light handle cover which is then adapted for use with the light handle 10 of this invention. One example of a manufacturer who makes light handle covers includes Devon Industries, Inc. of Chatsworth, Calif. This company makes and sells a product known as the "Lite Glove"®. As used with the light handle of this invention 10 and as further discussed below, the light handle cover 18 includes an opening 100 formed at the distal end thereof which allows the directed beam of light emanating from the light handle to reach its target. The light handle cover 18 can be made of a plastic for a disposable type of light handle cover, or the light handle cover may be made of aluminum or some other known metal whereby the light handle cover is resterilizable for multiple uses.

Because of the cylindrical shape of the light handle 10, and its symmetry with respect its longitudinal axis X—X, the light handle is well suited as a pointer for directing or pointing the directed beam of laser light onto a target.

Now referring to FIG. 3, the light handle 10 is illustrated to disclose its components. A distal adaptor 19 includes an adaptor housing 20, and a threaded well 22 for receiving the threaded proximal end 108 of the light handle cover 18. The opposite end of the distal adaptor 19 includes an external threaded portion 24 which may connect directly to a threaded well (not shown) within the central opaque area 16 of the light L. The threads 24 may be sized to fit the particular threaded well of the light L. Depending upon the type of light L used, the connection between the light handle and the light L may be a bayonet type connection, friction fit, or others. Thus, threaded portion 24 can be replaced with the desired type of fitting so to match the particular type of light L. The proximal end of the threaded portion 24 is capped or closed by a threaded proximal plug 26 which screws into internal thread (not shown) at the proximal end of the threaded portion 24. As discussed below, an optional additional adapter 90 may also be used.

A battery housing 30 is provided distally of the distal adaptor 19. The battery housing 30 is defined by a body 32, an exterior threaded proximal end 34 which is received in another threaded well (not shown) within the bore of distal adaptor 19 positioned proximally of threaded well 22. The housing 30 further includes an interior threaded distal end 36. The battery housing 30 is cylindrical shaped, and includes a bore extending completely therethrough.

A battery 38 is provided for powering the laser light source 60. The battery 38 is electrically connected to the laser source 60 via conducting strip 40, battery connector 42/44, and switch assembly 50. Male portion 42 of the battery connector may be removably connected with female portion 44 of the battery connector. The male portion 42 of the battery connector includes a set of conductive clips 43 which mate with corresponding structure on the female portion 44. The battery 38 simply fits between perpendicular extending contacts 45 of the conducting strip 40. The battery 38 along with the conducting strip 40 and battery connector 42/44 are inserted within the bore of the battery housing 30.

A distal cap 46 including threaded portion 48 is mounted over the distal end of the battery housing 30. One or more conductors 56 interconnect switch assembly 50 with connector 42/44. One or more conductors 56 may also interconnect the connector 42/44 with circuitry 64 of the laser light source 60. The switch assembly 50, in turn, connects directly to the laser light source 60. When the light handle is assembled, the switch assembly 50 and a pair of switch activation members 70 are positioned between the laser housing 76 and the battery housing 30.

Now also referring to FIGS. 4 and 5, the switch assembly 50 includes a pair of opposing micro-switches 52 which are mounted in opposing relationship on switch mounting board 54. An example of an acceptable laser source 60 includes a Class III visible diode laser (3 volts, 5 milli-watts, 635 nanometers). One manufacturer of such lasers is Quarton Inc., of City of Industry, Calif. This type of laser represents one which will produce a very bright laser light which is bright enough to overcome and be distinguished from surgical lights; however, the laser is not of such an intensity that will result in damage to the tissue of a patient, so long as exposure of the tissue to the laser is only of short duration. This type of laser produces a very clear and bright spot of light on the target in which it is viewed. The laser source 60 includes a projection window 62 from which the directed beam of laser light is projected. Typically, this type of laser source 60 includes its own control circuitry, shown as the circuit board 64.

The switch activation members 70 each include a pivot/rotation bore 72, and a travel bore 74. A plurality of screws 84 and bushings 86 are used to secure the components of the light handle. The distal cap 46 includes slots/cutouts 88 which receive corresponding screws 84. The screws 84 extend through openings 89 in the distal cap 46, through rotation bores 72 and travel bores 74, and are then screwed into corresponding threaded wells (not shown) formed on the periphery of the laser housing 76 at the proximal end thereof.

The travel bores 74 are elliptical in shape. Force applied in the direction of force arrows F allow the switch activation members to pivot or rotate about the screws 84 in pivot/rotation bores 72. The length or travel of the pivoting action is delimited by the available gap G between the interior edge of the bore 74 and the bushing 86. The switch activation members 70 are aligned such that their internal contacting surfaces 75 depress the corresponding micro-switches 52 when force is applied, thus activating the laser source 60 to produce a laser light beam. When no force is applied, the activation members 70 return to their normally open positions as shown in FIG. 4. One or both of these micro-switches 52 when depressed may activate the light source 60.

The laser housing 76 is the most distal component of the light handle, and includes a cylindrical body 80, a rounded tip 82, and an opening 78 which allows the directed beam of light from the laser source 60 to pass therethrough.

Optionally, an additional adaptor 90 may be used to connect the light handle 10 to the desired surgical light L. Proximal adaptor 90 simply includes a threaded proximal well 92 for receiving the external threaded portion 24, and external threaded portion 94 which can be modified in its size and thread configuration for connection to the desired type of surgical light. Because the construction of the distal adaptor 19 is somewhat more complex than the adaptor 90 (adaptor 19 also includes the set of internal threads for receiving the proximal end 34 of the battery housing) it may be more cost effective to use adaptor 90 and modify it for the particular type of surgical light used.

Now referring back to FIGS. 2 and 3, the light handle cover 18 is characterized by a handle portion 96 which may optionally include one or more exterior features such as ridges/slots 98. These features of the handle portion 96 are easily identified by touch. As desired, the ridges/slots 98 may be aligned over one of the switch activation members 70 so that a user simply has to feel for the ridges/slots 98, and then depress the light handle cover at or near the longitudinal location of the switch activation member 70 in order to activate/deactivate the laser light source. The opening 100 in the light handle cover allows the laser light source to pass therethrough. A shield 102 connects to the proximal end of the handle 96, and extends substantially perpendicular thereto. In order to reduce the size of the light handle cover 18 when it is packaged for shipment, tabs or ears 104 are provided which engage flanges 106, thus reducing the cross-sectional profile of the light handle cover. The light handle cover 18 is typically made of a plastic disposable material, and the shield portion 102 is of sufficient thinness which allows it to be bent so that tabs 104 may engage flanges 106. FIG. 2 shows the distal end of the light cover 18 extending beyond the distal end of the light handle 10, thus creating an offset or gap between the distal ends. This offset helps to prevent contamination that may enter through opening 100 from reaching the light handle 10. Although the light handle 10 is not sterile, use of the same light handle 10 in multiple procedures might cause a contamination problem if the distal end of the light handle was exposed to contamination and the distal end was placed in close proximity to the distal end of the light handle cover 18 whereby the contamination could travel back out through opening 100 into the sterile field. As mentioned above, the light handle cover 18 is secured to the light handle 10 by engaging the threaded end 108 of the light handle cover with the threaded well 22 of the light handle.

Referring to FIG. 6, an alternate source of power may be used in the form of solar electric generating assembly 110. The solar electric generating assembly 110 is a frusto-conical shaped component having a cylindrical shaped attachment flange 118 which mounts over adaptor housing 20. Referring also to FIG. 7, the solar electric generating assembly 110 includes the frusto conical shaped housing 112, a circumferential bead 114, and a thin film solar module 116 which is mounted over the proximal facing surface of the housing 112. As well as understood by those skilled in the art, the solar module 116 collects light thereon, and converts the light photons to electrical energy. The electrical charge created by the solar module 116 may be delivered to the switch assembly 50 by conductor 120, and an integral male connector 122 which plugs into the female portion 44 of the original battery connector. Accordingly, the battery 38, conducting strip 40, and male portion 42 of the battery connector are removed to allow the male connector 122 to provide voltage for the laser source 60.

Examples of commercially available thin film solar modules which may be used with the solar electric generating assembly 110 include various flexible solar modules as marketed and sold by Solar-World.com. A flexible solar module having a plastic substrate which is lightweight, flexible, and which produces a four volt/five milliamp output is adequate to power the laser source 60.

If the solar module assembly 110 is used as a power source, the light handle cover 18 is still easily usable with the invention. The proximal facing side of the shield 102 simply abuts the bead 114 of the solar assembly 110.

Preferably, the distal adaptor 19, battery housing 30, distal cap 46, switch activation members 70, and laser housing 76 are made of aluminum, stainless steel, or other commonly accepted metals used in surgical equipment. Aluminum is an excellent choice because it is lightweight and has high strength.

This invention has been described with respect to a particular disclosed preferred embodiment; however, it will be appreciated by those skilled in the art that various modifications and changes may be made within the spirit and scope of the invention.

What is claimed is:

1. A surgical light handle especially adapted for delivering a directed beam of light to a surgical area in order to align a surgical light, said light handle comprising:

a handle portion for grasping by a user, said handle portion connected to the surgical light;

a source of light integral with said handle portion for producing the directed beam of light projecting away from said handle portion at a distal end thereof, wherein the user can orient the surgical light by manipulating the positioning of the handle portion; and a power source integral with said light handle for powering said source of light.

2. A device, as claimed in claim 1, wherein:
said handle portion is cylindrical shaped.
3. A device, as claimed in claim 1, wherein:
said source of light is disposed near the distal end of said handle portion, and projects said beam of light away from said handle portion along a desired axis with respect to said handle portion.
4. A device, as claimed in claim 1, wherein:
said light handle extends along a longitudinal axis and said beam of light is projected away from said handle portion at the distal end thereof along said longitudinal axis.
5. A light handle especially adapted for delivering a directed beam of light to a work area, thus orienting an illuminating light used to illuminate the work area, said light handle comprising:
means for manipulating the illumination light to orient the illumination light on the work area, said means for manipulating being grasped by a user;
means for producing the directed beam of light integral with said means for manipulating; and
means for providing power communicating with said means for manipulating thereby powering said means for producing light.
6. A device, as claimed in claim 1, further including:
means attached to said handle portion for activating and deactivating the source of light.
7. A device, as claimed in claim 1, wherein:
said power source includes a battery disposed within said handle portion and electrically communicating with said source of fight.
8. A device, as claimed in claim 1, wherein:
said power source includes a solar module mounted on said handle portion, and electrically communicating with said source of light.
9. A device, as claimed in claim 1, further including:
a switch incorporated on said handle portion for activating and deactivating the source of light.
10. A device, as claimed in claim 1, wherein:
said source of light includes a laser light source housed within said handle portion for producing a directed laser light beam.
11. A device, as claimed in claim 10, wherein said switch further includes:
at least one micro-switch mounted within said handle portion; and
at least one switch activation member positioned adjacent said micro-switch and movable between a normally open position, and a closed position which operates said micro-switch to activate the source of light to produce the directed beam of light.
12. A device, as claimed in claim 11, wherein:
said at least one micro-switch includes a pair of opposing micro-switches, and said at least one switch activation member includes a pair of opposing switch activation members wherein moving at least one of said pair of opposing switch activation members to the closed position results in operation of at least one of said micro-switches for activating said source of light.

13. A device, as claimed in claim 1, further including:
a cover for covering said handle portion, said cover substantially conforming in shape to said handle portion.
14. A device, as claimed in claim 13, wherein:
said cover includes a distal end portion, and an opening formed in said distal end portion enabling said directed beam of light to pass therethrough.
15. A method of orienting an illuminating light on a work area, said method comprising the steps of:
providing an illuminating light producing a light pattern for illuminating a desired work area;
attaching a means to the illuminating light for orienting the illumination light to project light to a desired location within the work area;
incorporating a light source producing a directed beam of light within said means for orienting, the directed beam of light being differentiated from the light produced by the illuminating light; and
manipulating the means for orienting to direct the directed beam of light to the desired location within the work area thus orienting the light pattern of the illuminating light.
16. A method, as claimed in claim 15, wherein:
said means for orienting includes a handle attached to the illuminating light.
17. A method, as claimed in claim 15, further including the step of:
powering said light source by a battery.
18. A method, as claimed in claim 15, further including the step of:
powering said light source by a solar module which receives light from the illuminating light.
19. A light handle especially adapted for delivering a directed beam of light to a work area, thus orienting an illuminating light used to illuminate the work area, said light handle comprising:
a handle portion for grasping by a user, and releaseably connected to the illuminating light;
a source of light producing the directed beam of light mounted within said handle portion, wherein manipulating the handle portion to project the directed beam of light on a target within the work area orients the illuminating light on the work area; and
a power source integral with said handle portion for powering said source of light.
20. A light handle especially adapted for delivering a directed beam of light to a work area, thus orienting an illuminating light used to illuminate the work area, said light handle comprising:
means for manipulating the illumination light to orient the illumination light on the work area, said means for manipulating being grasped by a user;
a source of light producing the directed beam of light mounted to said means for manipulating; and
a power source communicating with said means for manipulating for powering said source of light.

* * * * *

UNITED STATES PATENT AND TRADEMARK OFFICE
CERTIFICATE OF CORRECTION

PATENT NO. : 6,715,904 B2
DATED : April 6, 2004
INVENTOR(S) : Michael L. Naughton It is certified that error appears in the above-identified patent and that said Letters Patent is hereby corrected as shown below:

Column 7,
Line 31, please delete "fight" and replace with -- light --.

Signed and Sealed this

Seventh Day of September, 2004

JON W. DUDAS
*Director of the United States Patent and Trademark Office*